United States Patent [19]
Dunn et al.

[11] Patent Number: 5,449,374
[45] Date of Patent: Sep. 12, 1995

[54] TISSUE SPREADING FORCEPS

[75] Inventors: Raymond M. Dunn, Shrewsbury; Allen H. Hoffman, Sterling; Richard Doppler; Marc G. Casseres, both of Worcester, all of Mass.

[73] Assignees: University of Massachusetts Medical Center; Worcester Polytechnic Institute, both of Worcester, Mass.

[21] Appl. No.: 42,397

[22] Filed: Apr. 1, 1993

[51] Int. Cl.⁶ .............................................. A61B 17/28
[52] U.S. Cl. ..................................... 606/208; 606/210; 294/992; 600/214; 600/216
[58] Field of Search .................. 128/20; 606/152, 153, 606/205–211, 216; 294/99.2

[56] References Cited

U.S. PATENT DOCUMENTS

| | | |
|---|---|---|
| 2,965,900 | 12/1960 | Inokouchi ........................... 606/153 |
| 4,165,747 | 8/1979 | Bermant ............................... 606/153 |
| 4,747,407 | 5/1988 | Liu et al. ............................. 606/153 |

FOREIGN PATENT DOCUMENTS

| | | | |
|---|---|---|---|
| 35357 | 3/1930 | France | ................... 606/208 |
| 641398 | 6/1962 | Italy | ..................... 606/208 |

OTHER PUBLICATIONS

Frankel, David H., M.D., "The Use of a Combination Skin Hook and Tissue Forceps: A New Instrument for Dermatologic Surgery (Frankel-Adson Forceps*)," J. Dermatol. Surg. Oncol. 14:5:497–499 (1988).
Grande et al., "Instrumentation for the Dermatologic Surgeon," J. Dermatol Surg Oncol 15:3:288–297 (1989).

*Primary Examiner*—Stephen C. Pellegrino
*Assistant Examiner*—William Lewis
*Attorney, Agent, or Firm*—Hamilton, Brooks, Smith & Reynolds

[57] ABSTRACT

A tissue spreading forceps for gripping and spreading tissue include two gripping members which are secured to each other by a spring and are rotatable in relation to each other about a pivot. Initial pressure to the spring causes the gripping members to close and grip tissue at two locations. Additional pressure applied to the spring causes the gripping members to spread apart in relation to each other, thereby spreading the tissue.

29 Claims, 3 Drawing Sheets

TISSUE SPREADING FORCEPS

BACKGROUND

During suturing procedures for closing wounds, a surgeon must bring the wound edges into close proximity to each other to facilitate the placement of the suture. Either stitches or staples typically serve as the suture. Likewise, during plastic and reconstructive surgery, the skin must be stretched so that the location of the incision edges can be approximated before any excess skin is removed or excised. Excess skin is typically removed with a cutting instrument such as a scalpel or surgical scissors. This skin manipulation, accomplished with the use of forceps, must be performed with extreme care in order to avoid damage to the skin which may cause the formation of scar tissue.

The high elasticity of human tissue makes current methods of stabilizing of wound edges utilizing standard tissue grasping forceps inadequate. Standard forceps have only one grasp site and tend to deform tissue when tension is applied by the forceps to the tissue. This deformation makes it difficult to excise the tissue to obtain parallel wound edges. This problem is typically alleviated by using two separate forceps to grasp the skin at two distinct sites. The use of two forceps provide for uniform skin stretching while allowing the application of tension between the grasping sites. This tension between the grasping sites enables the surgeon to hold the wound edge in a parallel orientation with respect to the opposite wound edge. In order to properly spread the tissue, an assistant is required to help the surgeon perform the procedure because the surgeon must have at least one hand free. The surgeon uses the free hand to apply a suture or to cut excess tissue away with a cutting instrument.

SUMMARY OF THE INVENTION

A drawback of enlisting the aid of an assistant to spread tissue is that the working area can become crowded and the visibility reduced. Additionally, mistakes can be made if there are miscommunications between the surgeon and the assistant. Furthermore, an assistant is often not available in many minor or emergency procedures. Accordingly, there is a need for a device which can enable a surgeon to grasp and spread tissue without the help of an assistant and a second pair of forceps.

The tissue spreading forceps of the present invention include a first gripping member for gripping tissue at a first location and a second gripping member for gripping tissue at a second location. A joint connects the first and second gripping members such that the first and second gripping members can be spread apart.

In a preferred embodiment, a spring secures the first and second gripping members together. Additionally, the joint is a pivot which rotatably connects the first and second gripping members together. When a surgeon applies an initial level of pressure to the spring with his or her thumb, the first and second gripping members close and grasp tissue at two different locations. Additional pressure to the spring laterally separates the first and second gripping members apart from each other thereby spreading and stabilizing the gripped tissue. Once the tissue has been stabilized, a suture can be applied to the wound or excess tissue can be removed with a cutting instrument held in the other hand of the surgeon.

The present invention provides tissue spreading forceps which allow greater ease and precision in tissue handling for surgical procedures such as wound trimming and closing wounds by allowing a single surgeon to perform the procedure. Both the closure of the gripping members about the tissue and the spreading of the tissue is performed in one simple motion by applying pressure to the spring with the surgeon's thumb. This allows the surgeon to concentrate on the actual surgical procedure to be performed on the tissue rather than concentrating on the spreading of the tissue.

BRIEF DESCRIPTION OF THE DRAWINGS

The foregoing and other objects, features and advantages of the invention will be apparent from the following more particular description of preferred embodiments of the drawings in which like reference characters refer to the same parts throughout the different views. The drawings are not necessarily to scale, emphasis instead being placed upon illustrating the principles of the invention.

DETAILED DESCRIPTION OF THE PREFERRED EMBODIMENT

Figure 1:
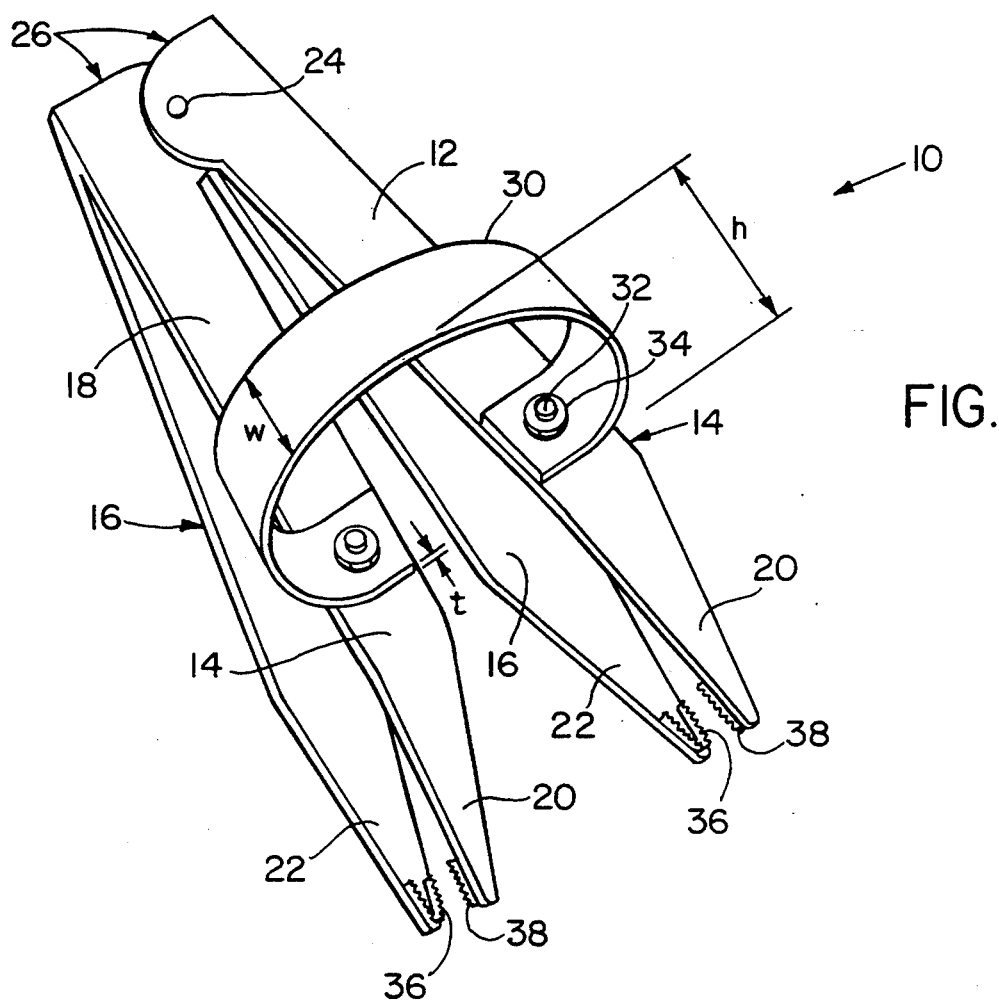
FIG. 1 is a perspective view of a preferred embodiment of the tissue spreading forceps of the present invention.

In FIG. 1, forceps 10 are a hand operated tissue spreading instrument which has two gripping members 12 and 18 for gripping and spreading tissue between two separate sites in order to facilitate surgical procedures such as suturing or tissue excising procedures. Forceps 10 are useful for stretching skin as well as most other types of body tissues such as muscle or membranes.

Figure 2:
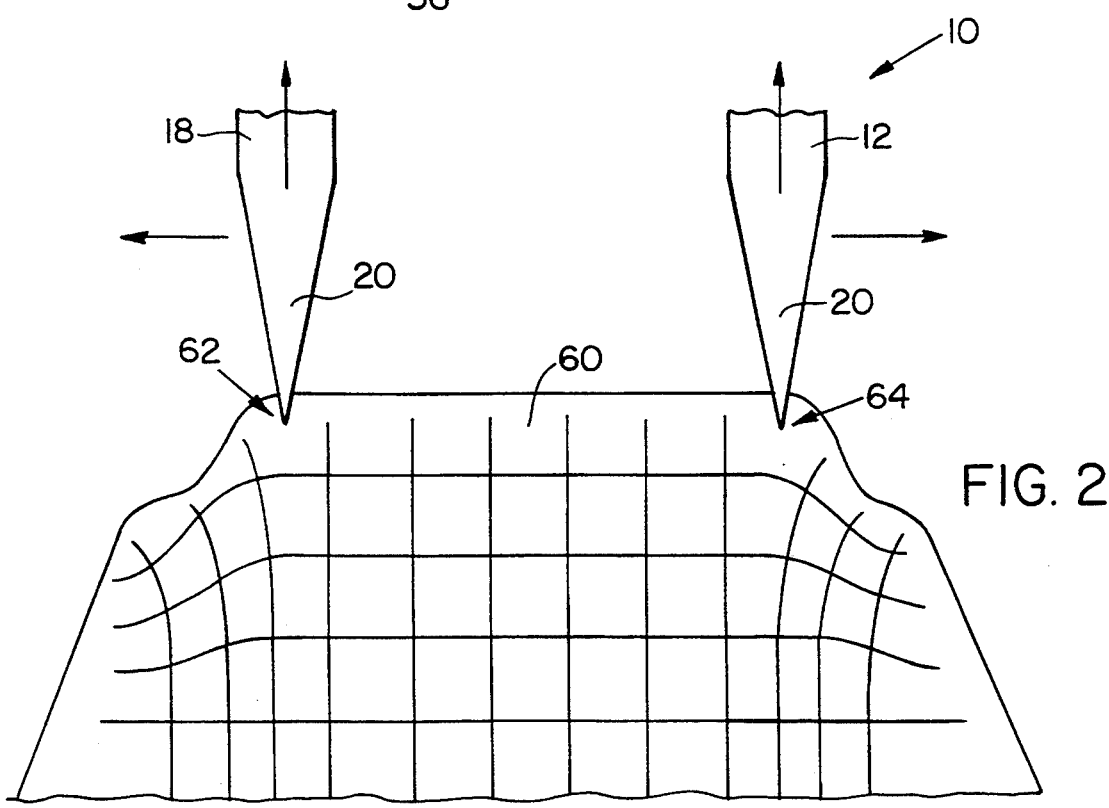
FIG. 2 depicts the gripping and spreading of tissue by the present invention.

In operation, forceps 10 are held in the hand of a surgeon with the thumb positioned over spring 30 and two fingers positioned under gripping members 12 and 18. Forceps 10 are then positioned in close proximity to the tissue to which a surgical procedure is to be performed. An initial level of pressure is applied by the surgeon's thumb to spring 30 which causes the jaws (described in more detail below) of gripping members 12 and 18 to close about and to grip the desired tissue 60 (FIG. 2). Tissue 60 is gripped at a first location 64 and at a second location 62. When additional pressure is applied to spring 30, spring 30 deflects and lengthens. Spring 30 is stiffer than the gripping members so that the gripping members will close before spring 30 deflects. When spring 30 lengthens, gripping members 12 and 18 are spread laterally apart in the direction of the arrows while at the same time pivoting about hinge 2 thereby spreading tissue 60. This stabilizes tissue 60 so that the surgeon can perform the desired surgical procedure to the tissue with the surgeon's free hand. Additionally, tissue 60 can be spread in the direction of the vertical arrows by pulling tissue 60 in that direction with forceps 10.

The surgical procedures which can be performed to tissue with the aid of forceps 10 include joining wound edges in close proximity to each other so that stitches or staples can be applied to close the wound. Additional surgical procedures include cutting excess tissue during reconstructive surgery with a scalpel, surgical scissors, or a laser. The cutting instrument which is to be used can depend upon the type and thickness of the tissue.

A more detailed description of forceps 10 is given below.

Gripping members 12 and 18 have a top leg 14 and a bottom leg 16. Top legs 14 and bottom legs 16 are separated from each other by a gap and are joined together at ends 26. Gripping members 12 and 18 grasp tissue at jaws 36 and 38 when top leg 14 and bottom leg 16 are moved towards each other to contact the tissue. A bar can also be secured to bottom legs 16 connecting gripping members 12 and 18 so that forceps 10 can rest comfortably in the hand of a surgeon. In the preferred embodiment, gripping members 12 and 18 are approximately 4½ to 5 inches long and are preferably made of flexible surgical grade stainless steel. Alternatively, gripping members 12 and 18 can be of other suitable lengths depending upon the application and can be made of other suitable materials such as medical grade plastic. For example, the forceps used in eye surgery would typically be shorter than the forceps used in plastic or reconstructive surgery.

Hinge 24 rotatably connects gripping members 12 and 18 to each other. Hinge 24 allows gripping members 12 and 18 to pivot relative to each other so that the tips 20 of the gripping members can be spread apart laterally.

Tips 20 and 22 are located at the ends of legs 14 and 16 respectively. Tips 20 and 22 are bent towards each other slightly such that jaws 38 and 36 can contact and grip tissue when legs 14 and 16 are closed. Tips 20 and 22 are depicted as being tapered but can be alternatively of other suitable shapes depending upon the particular application as depicted in FIGS. 5–8.

Jaws 36 and 38 have a number of small teeth which are arranged in an arched pattern. The arched pattern of teeth can be a circular or semicircular pattern. An arched arrangement of the teeth provides forceps 10 with a biaxial gripping ability which allows forceps 10 to pull and spread tissue in two directions as depicted in FIG. 2.

Arched spring 30 is secured to the top legs 14 of gripping members 12 and 18 by screws 32 and nuts 34. In the preferred embodiment, spring 30 is positioned approximately two thirds the length of leg 14 away from hinge 24 so that spring 30 is near the tips 20 of gripping members of 12 and 18. Alternatively, spring 30 can be positioned at other suitable locations along legs 14. Additionally, spring 30 can be secured to legs 14 by other suitable means such as with rivets, adhesives or welds.

Spring 30 is of sufficient stiffness so that when the surgeon initially applies thumb pressure to spring 30, gripping members 12 and 18 will close without causing spring 30 to deflect. For example, for a 5 inch long pair of forceps, a force of 300 grams on spring 30 is generally necessary to close gripping members 12 and 18. An additional force of 100 grams is required to deflect spring 30 once the gripping members 12 and 18 are closed. Therefore, a force of 400 grams is required to deflect spring 30. The 100 gram difference between the closing and spreading forces applied to spring 30 provides forceps 10 with sufficient gripping force to grip tissue. Gripping members 12 and 18 can be designed so that gripping members 12 and 18 close when either higher or lower forces are applied to spring 30 in order to change the gripping force. In the preferred embodiment, spring 30 is made of a thermal plastic which has been heated and molded into an arched shape. Alternatively, spring 30 may be made of other suitable spring materials. In another preferred embodiment, spring 30 is made of stainless steel. The spring may also be of any curved shape and be of variable width (w).

Figure 3:
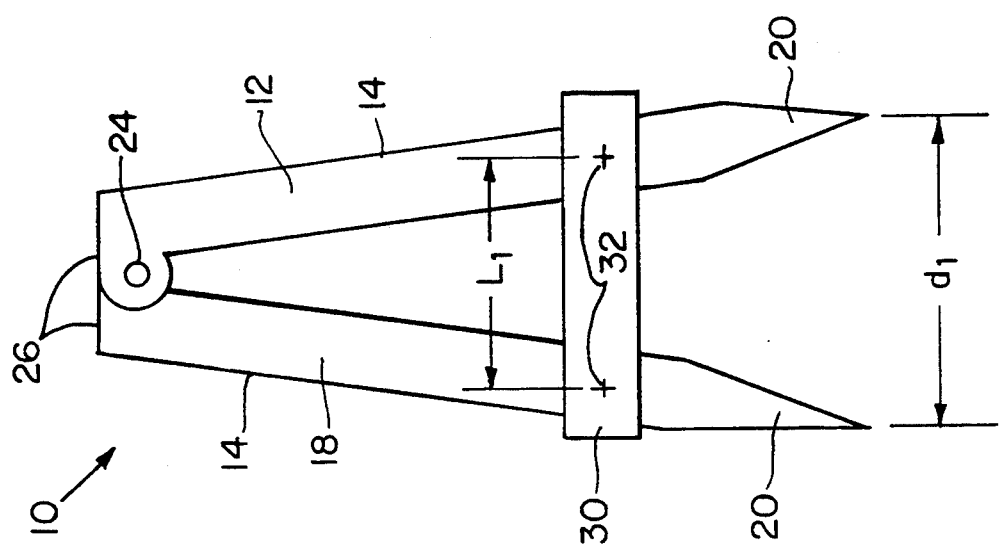
FIG. 3 is a plan view of the tissue spreading forceps in its natural state.

For 5 inch long forceps, spring 30 can have a width w of 10 mm, a thickness t of 0.75 mm, a height of 20 mm, a modulus of elasticity of 0.83 GPA and a length $L_1$ of approximately 7 mm between screws 32. A 5 inch long forceps having a spring 30 of these dimensions provides an initial distance $d_1$ between the tips 20 of forceps 10 of 10 mm (FIG. 3) which is suitable for most wound suturing and tissue excising applications.

Figure 4:
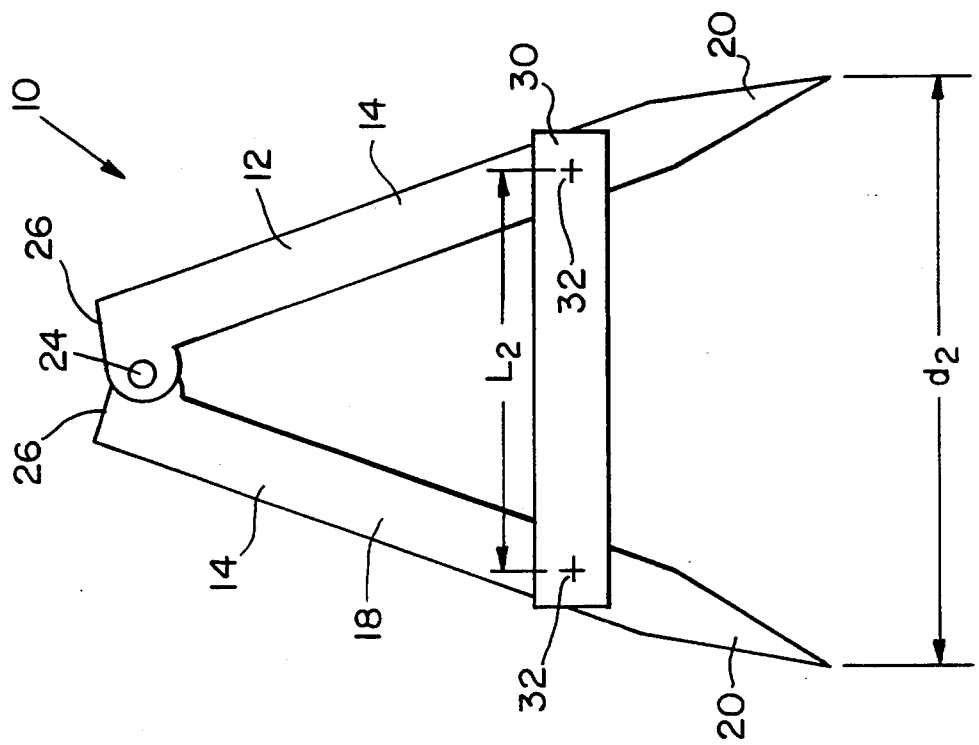
FIG. 4 is a plan view of the tissue spreading forceps in which the gripping members are spread apart.

When spring 30 is deflected so that gripping members 12 and 18 are spread apart as depicted in FIG. 4, the final distance $d_2$ between tips 20 is preferably about double the initial distance $d_1$, in order to provide a suitable tissue spread. Therefore, for example, for a 5 inch long pair of forceps having an initial distance $d_1$ of 10 mm, $d_2$ will be approximately 20 mm. At this distance, deflected length $L_2$ of spring 30 becomes approximately 14 mm. Although examples of spring dimensions have been given for 5 inch long forceps, spring dimensions and properties are variable depending on the size and design of the forceps as well as the application to which the forceps are being used.

FIGS. 5 through 8 depict other preferred jaw configurations for forceps 10.

Figure 5:
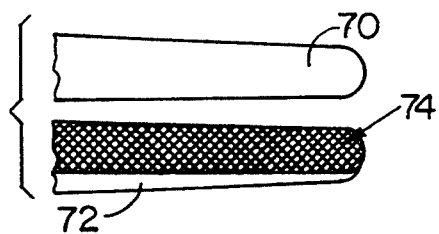
FIG. 5 is a perspective view of a jaw with a textured surface.

In FIG. 5, jaws 70 and 72 have a serrated gripping surface 74. Serrated jaws cause relatively little tissue damage under low grasping force and limited tissue tension. Serrated jaws provide adequate gripping traction while handling tissue gently enough to minimize trauma.

Figure 6:
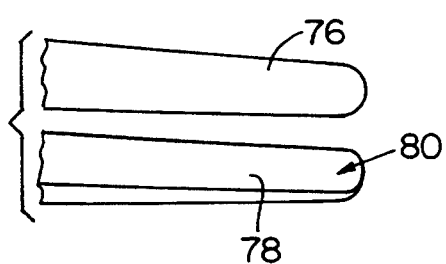
FIG. 6 is a perspective view of a jaw having a smooth surface.

In FIG. 6, jaws 76 and 78 have a smooth gripping surface 80. A smooth gripping surface is desirable for further minimizing damage to tissue that is being grasped. Smooth forceps provide gentle handling of tissue which is essential for proper healing and good cosmetic result.

Figure 7:
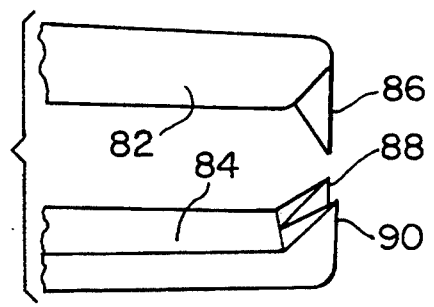
FIG. 7 is a perspective view of a jaw having three teeth.

In FIG. 7, jaw 82 has a single tooth 86 which mates with teeth 88 and 90 of jaw 84. Toothed forceps are desirable when a high pulling force is required.

Figure 8:
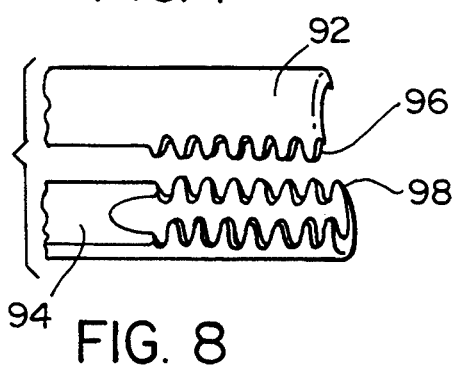
FIG. 8 is a perspective view of a jaw having multiple teeth.

In FIG. 8, jaws 92 and 94 have multiple mating teeth 96 and 98 which is a combination of serrated and toothed designs. The smaller multiple teeth allows force on the tissue to be evenly applied over the grasped tissue area. This is useful in areas of thick subcutaneous tissue where the serrated tooth forceps are too fine to grasp the tissue adequately.

Figure 9:
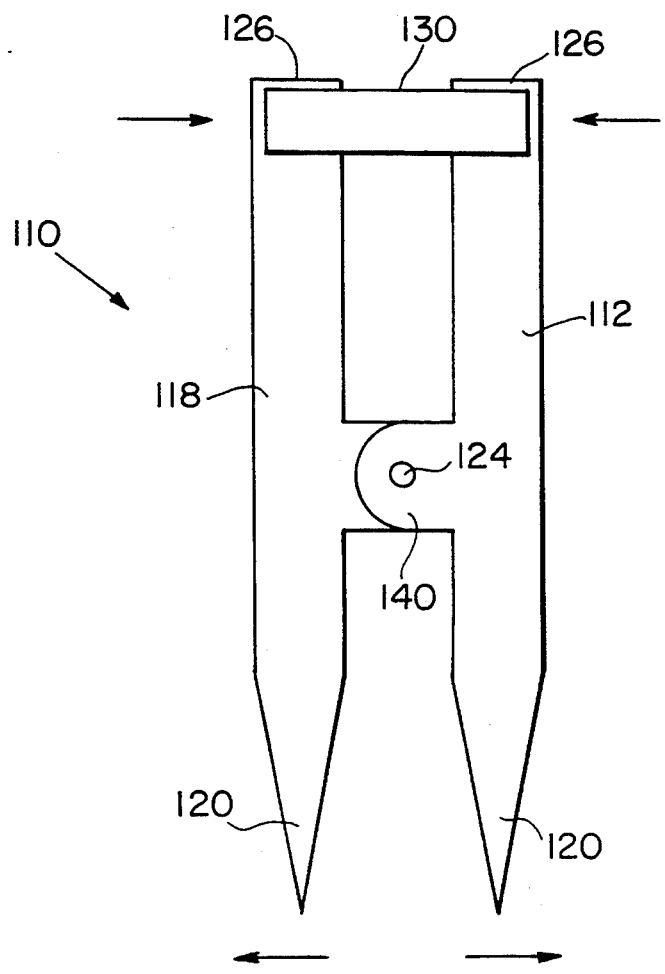
FIG. 9 is a plan view of another preferred embodiment of the present invention.

FIG. 9 depicts another preferred embodiment of the present invention. Forceps 110 have two gripping members 112 and 118 respectively. Gripping members 112 and 118 are similar to gripping members 12 and 18 in FIG. 1 in that gripping members 112 and 118 include two legs which are secured to each other at ends 126. A hinge 124 rotatably connects gripping members 112 and 118 approximately at the midpoint of the gripping members. A spring 130 secures the ends 126 of gripping members 112 and 118 together. Spring 130 is an arched spring member similar to spring 30 in FIG. 1. Alternatively, spring 130 can be a helical spring.

In operation, pressure from the surgeon's thumb is applied to region 140 of forceps 110 thereby closing the jaws of gripping members 112 and 118 to grasp a desired piece of tissue at two separate locations. In order to spread the gripped tissue, the surgeon's hand squeezes the ends 126 in the direction of the arrows. This laterally separates tips 120 apart thereby spreading the gripped tissue. Once the tissue is stabilized, the surgeon can perform the desired surgical procedure to the tissue.

An optional locking mechanism can be added to forceps 10 and 110 to lock the gripping members in a spread position to facilitate suturing procedures. Additionally, hinges 24 and 124 can be replaced with a sliding joint.

Equivalents

While this invention has been particularly shown and described with references to preferred embodiments thereof, it will be understood by those skilled in the art that various changes and form and details may be made therein without departing from the spirit and scope of the invention as defined by the dependent claims.

The invention claimed is:

1. Tissue spreading forceps comprising:
   a first gripping member having proximal and distal ends, the first gripping member having a first jaw at the distal end for gripping tissue at a first location;
   a second gripping member having proximal and distal ends, the second gripping member having a second jaw at the distal end for gripping tissue at a second location;
   a joint connecting the first and second gripping members such that the distance between the first and second jaws can be varied, wherein the joint is a pivot for rotatably connecting the first and second gripping members together; and
   a spring secured to the first and second gripping members such that pressure to the spring closes the first and second jaws and spreads the laws of the first and second gripping members apart from each other.

2. The forceps of claim 1 wherein the spring comprises an arched spring member.

3. The forceps of claim 2 wherein the spring is secured near the distal end of the gripping members.

4. The forceps of claim 1 wherein the pivot secures the first and second gripping members at the proximal ends of the first and second gripping members.

5. The forceps of claim 1 wherein the gripping members comprise:
   a first leg having a proximal and distal end; and
   a second leg having a proximal and distal end, the first and second legs being secured to each other at their proximal ends.

6. The forceps of claim 1 wherein the jaws have a smooth gripping surface.

7. The forceps of claim 1 wherein the jaws have a textured gripping surface.

8. The forceps of claim 1 wherein the jaws have a toothed gripping surface.

9. The forceps of claim 8 wherein the toothed gripping surface is in an arched pattern.

10. The forceps of claim 1 wherein the pivot rotatably connects the first and second gripping members midway between the proximal and distal ends.

11. The forceps of claim 10 wherein the spring is secured to the first and second gripping members at the proximal end of the gripping members.

12. Tissue spreading forceps comprising:
   a first gripping member for gripping tissue at a first location, the first gripping member having proximal and distal ends;
   a second gripping member for gripping tissue at a second location, the second gripping member having proximal and distal ends, the first and second gripping members being connected at a joint such that the distal ends of the gripping members are spreadable from each other, wherein the joint is a pivot for rotatably connecting the first and second gripping members together; and
   a spring secured to the first and second gripping members, such that pressure to the spring closes the first and second gripping members as well as spreads the distal ends of the first and second gripping members apart from each other.

13. The forceps of claim 12 wherein the spring comprises an arched spring member.

14. The forceps of claim 12 wherein the pivot secures the first and second gripping members at the proximal ends of the gripping members.

15. The forceps of claim 12 wherein the spring is secured near the distal end of the gripping members.

16. The forceps of claim 12 wherein the gripping members comprise:
   a first leg having a proximal and distal end; and
   a second leg having a proximal and distal end, the first and second legs being secured to each other at their proximal ends.

17. The forceps of claim 12 wherein the gripping members have a smooth gripping surface.

18. The forceps of claim 12 wherein the gripping members have a textured gripping surface.

19. The forceps of claim 12 wherein the gripping members have a toothed gripping surface.

20. The forceps of claim 19 wherein the toothed gripping surface is in an arched pattern.

21. The forceps of claim 12 wherein the pivot rotatably connects first and second gripping members midway between their proximal and distal ends.

22. The forceps of claim 12 wherein the spring secures the first and second gripping members together at their proximal ends.

23. A method of spreading tissue comprising:
   gripping the tissue with a pair of forceps, the forceps having a first gripping member for gripping tissue at a first location and a second gripping member for gripping tissue at a second location; an initial level of pressure applied to the gripping members closing the first and second gripping members; and
   applying an additional level of pressure to the first and second gripping members spreading the first and second gripping members apart thereby spreading the gripped tissue apart.

24. The method of claim 23 wherein the pressure is applied to a spring secured to the first and second gripping members.

25. The method of claim 23 wherein the pressure is applied to a spring secured to the first and second gripping members.

26. Tissue spreading forceps comprising:
a first gripping member having proximal and distal ends, the first gripping member having a first jaw at the distal end for gripping tissue at a first location;
a second gripping member having proximal and distal ends, the second gripping member having a second jaw at the distal end for gripping tissue at a second location;
a joint connecting the first and second gripping members such that the distance between the first and second jaws can be varied; and
a connecting member coupling the first and second gripping members together for closing first and second jaws and spreading the jaws of the first and second gripping members apart from each other when pressure is exerted on the connecting member.

27. Tissue spreading forceps comprising:
a first gripping member for gripping tissue at a first location, the first gripping member having proximal and distal ends;
a second gripping member for gripping tissue at a second location, the second gripping member having proximal and distal ends, the first and second gripping members being connected at a joint such that the distal ends of the gripping members are spreadable from each other; and
a connecting member coupling the first and second gripping members together for closing the first and second gripping members and spreading the distal ends of the first and second gripping members apart from each other when pressure is exerted on the connecting member.

28. Tissue spreading forceps comprising:
a first gripping member for gripping tissue at a first location, the first gripping member having proximal and distal ends;
a second gripping member for gripping tissue at a second location, the second gripping member having proximal and distal ends, the first and second gripping members being coupled such that the distal ends of the gripping members are spreadable from each other; and
an actuator linked to the first and second gripping members for closing the first and second gripping members and spreading the distal ends of the first and second gripping members apart from each other.

29. A method of spreading tissue with a pair of forceps comprising the steps of:
gripping the tissue with the forceps, the forceps having a first gripping member for gripping tissue at a first location and a second gripping member for gripping tissue at a second location, the gripping members gripping the tissue upon actuation of an acutator linked to the first and second gripping members; and
spreading the first and second gripping members apart, thereby spreading the gripped tissue apart upon further actuation of the actuator.

* * * * *